United States Patent
Su et al.

(10) Patent No.: US 9,181,159 B2
(45) Date of Patent: Nov. 10, 2015

(54) METHOD FOR COPRODUCING ISOBUTENE AND MTBE FROM TERT-BUTANOL MIXTURE IN A CATALYTIC DISTILLATION COLUMN

(71) Applicant: CPC CORPORATION, TAIWAN, Taipei (TW)

(72) Inventors: Wei-Bin Su, Chiayi (TW); Karl Tze-Tang Chuang, Chiayi (TW); Cheng-Tsung Hong, Chiayi (TW); Jeng-Cheng Lee, Chiayi (TW)

(73) Assignee: CPC Corporation, Taiwan, Taipei (TW)

( * ) Notice: Subject to any disclaimer, the term of this patent is extended or adjusted under 35 U.S.C. 154(b) by 137 days.

(21) Appl. No.: 14/161,903

(22) Filed: Jan. 23, 2014

(65) Prior Publication Data

US 2015/0203426 A1   Jul. 23, 2015

(51) Int. Cl.
  *C07C 41/09*   (2006.01)
  *C07C 1/22*    (2006.01)

(52) U.S. Cl.
  CPC . *C07C 41/09* (2013.01); *C07C 1/22* (2013.01); *C07C 2527/03* (2013.01)

(58) Field of Classification Search
  CPC ........ C07C 41/09; C07C 2527/03; C07C 1/24
  See application file for complete search history.

(56) References Cited

U.S. PATENT DOCUMENTS

| | | |
|---|---|---|
| 4,423,271 A | 12/1983 | Obenaus et al. |
| 4,918,244 A | 4/1990 | Nelson et al. |
| 4,925,989 A | 5/1990 | Hagan et al. |
| 5,081,318 A | 1/1992 | Knifton |
| 5,099,072 A | 3/1992 | Knifton |
| 5,313,006 A | 5/1994 | Knifton |
| 5,523,061 A * | 6/1996 | Hao et al. ............ 422/605 |
| 5,625,109 A | 4/1997 | Gupta |
| 5,705,711 A | 1/1998 | Preston |
| 5,741,953 A | 4/1998 | Preston |
| 5,811,620 A | 9/1998 | Knifton et al. |
| 5,849,971 A | 12/1998 | Sakuth et al. |
| 5,856,588 A | 1/1999 | Dai et al. |

OTHER PUBLICATIONS

Mohammed H. Matouq and Shigeo Goto; Kinetics of Liquid Phase Synthesis of Methyl tert-Butyl Ether from tert-Butyl Alcohol and Methanol Catalyzed by Ion Exchange Resin; International Journal of Chemical Kinetics, vol. 25, pp. 825-831 (1993).

* cited by examiner

*Primary Examiner* — Rosalynd Keys
(74) *Attorney, Agent, or Firm* — Rosenberg, Klein & Lee

(57) ABSTRACT

This invention describes a method for co-producing isobutene and methyl tert-butyl ether in a catalytic distillation column, wherein contacting with solid acid catalysts the charged tert-butanol mixture undergoes dehydration and etherification. The mixture of isobutene and methyl tert-butyl ether withdrawn from the column top can be further separated, thus high purity isobutene and fuel-additive methyl tert-butyl ether are obtained.

20 Claims, 5 Drawing Sheets

METHOD FOR COPRODUCING ISOBUTENE AND MTBE FROM TERT-BUTANOL MIXTURE IN A CATALYTIC DISTILLATION COLUMN

FIELD OF THE INVENTION

The present invention relates to a process for the co-preparation of isobutene and methyl tert-butyl ether (MTBE) from a mixture of tert-butanol (TBA) and methanol. The process is carried out in a catalytic distillation column, followed by wash columns to remove methanol and a distillation column to separate isobutene and MTBE.

BACKGROUND OF THE INVENTION

Isobutene is the raw material to manufacture alkylate, MTBE, diisobutylene, polyisobutene, methacrylic acid, butylated phenols, etc. There are three sources of isobutene: catalytic cracking, steam cracking, and dehydrogenation of butanes. However, in those processes isobutene is always produced as a mixture of C4s. It is costly to produce high purity isobutene from those mixtures due to their close boiling points.

There are currently three important processes for the production of high purity isobutene: (1) the extraction process using an acid to separate isobutene, (2) the dehydration of tert-butanol, and (3) the cracking of MTBE. The expected demand for MTBE precludes the third route for isobutene production. MTBE is more valuable than TBA due to its huge demand as an additive in gasoline fuel. TBA will be an important source of isobutene and MTBE. Large quantities of TBA obtained as a by-product from propylene oxide (PO) plants become an important source for isobutene and MTBE.

U.S. Pat. No. 4,918,244 discloses a one-step process for preparing MTBE. TBA and methanol are continuously fed to a rectification tower having a packed solid-acid catalyst bed where the TBA and methanol react in the presence of the catalyst to produce MTBE. Stream data show that MTBE was the only product and isobutene was not produced in the claimed process. U.S. Pat. No. 4,925,989 discloses a process for preparing MTBE. TBA, isobutene and methanol are continuously fed into a combination reactor distillation tower having a packed sulfonic acid resin catalyst beds. However, a third raw material of isobutene is required to enhance MTBE yield in this invention. Although isobutene could be recovered from the product, but it eventually consumed and not produced. Consequently, isobutene is not co-produced in the disclosure of these two patents.

Integrating a prereactor and a CD column, the disclosed processes for MTBE production in U.S. Pat. Nos. 5,705,711 and 5,741,953 also indicate that isobutene is not co-produced. In the latter case, the isobutene is recovered as a mixture together with TBA and methanol, and recycled to the primary reactor to produce MTBE. Also, the CD column behind a prereactor is not charged with fresh TBA/methanol and is an auxiliary equipment to enhance MTBE yield. The molar ratio of methanol-to-TBA at the prereactor reaches 2.0 so that the energy consumption in recycling methanol is very high.

A serious of acid catalysts were disclosed for converting TBA to MTBE, such as ion-exchange resin, fluorosulfonic acid-treated Y-zeolite and acidic montmorillonite silica-alumina (U.S. Pat. Nos. 5,081,318 and 5,099,072). TBA and methanol were contacted with these catalysts and mostly first-stage converted to isobutene and MTBE. A fluoride-treated Y-zeolite or silicoaluminophosphate (U.S. Pat. Nos. 5,313,006 and 5,856,588) are claimed to have the ability to improve MTBE yield via the second-stage etherification of the unreacted or recovered TBA.

On the other hand, following patents are focus on the isobutene production via TBA dehydration. U.S. Pat. No. 4,423,271 discloses a method, which uses ion exchange resin as catalyst to dehydrate aqueous TBA in a fixed bed. U.S. Pat. No. 5,811,620 discloses a TBA dehydration method for producing isobutene via a reactive distillation column packed with fluoride-treated catalyst. A similar method is also disclosed in U.S. Pat. No. 5,849,971. However, no methanol is fed to the column and MTBE cannot be cogenerated with isobutene. In order to manufacture MTBE, an etherification process is required to follow with these TBA dehydration process.

The above methods are limited for industrial application. For example, TBA at high purity is solid state as temperature is below 25° C. The transportation for market trade is inconvenient. Also, these patented processes should be localized around the PO process or isobutene hydration process to avoid the TBA transportation problem.

The kinetics of liquid phase synthesis of MTBE from TBA and methanol catalyzed by ion exchange resin is proposed by Matouq and Goto, Int. J. Chem. Kinnet., 1993, 25, 825-831. In their report, the TBA and methanol undergo etherification and dehydration simultaneously over Amberlyst 15 such that MTBE and isobutene can be co-produced.

SUMMARY

The freezing point of TBA at ambient pressure is about 25° C. Its transportation is very inconvenient, especially for shipping for long distance. As TBA is used as raw material, the location for manufacturing isobutene and its derivatives should be close to a PO plant or isobutene hydration plant. Then the downstream products can be easily distributed to customers. Otherwise, considering market demand and production flexibility, locally produced isobutene should be shipped with pressurized vessel for downstream processing. The isobutene transportation is costly.

The object of the present invention is to lower the freezing point of TBA by mixing it with methanol, such that TBA can be shipped cheaply anywhere. This mixture can be directly charged to a catalytic distillation column, wherein is equipped with acid catalyst, e.g. Amberlyst 35, to undergo etherification and dehydration, simultaneously. Following water wash and distillation, the main products are isobutene and MTBE. Another object of the invention is to co-produce isobutene and MTBE from the mixture of TBA and methanol.

When methanol concentration is higher than 8.22 wt %, the freezing point of TBA mixture is below zero degree C. Since the higher the methanol concentration in the TBA mixture the lower is the freezing point, the concentration can be adjusted according to the ambient temperature during shipping of the mixture. The process allows the use of this mixture as received. This is called the first feed point of the CD column. Additional methanol, if required can also be fed to the CD column as the second feed. The variable feed concentration results in the flexibility to produce a wide range of isobutene-to-MTBE ratio through this invented process.

DETAILED DESCRIPTION

In order to make the structure and characteristics as well as the effectiveness of the present invention to be further understood and recognized, the detailed description of the present invention is provided as follows along with embodiments and accompanying figures.

Figure 1:
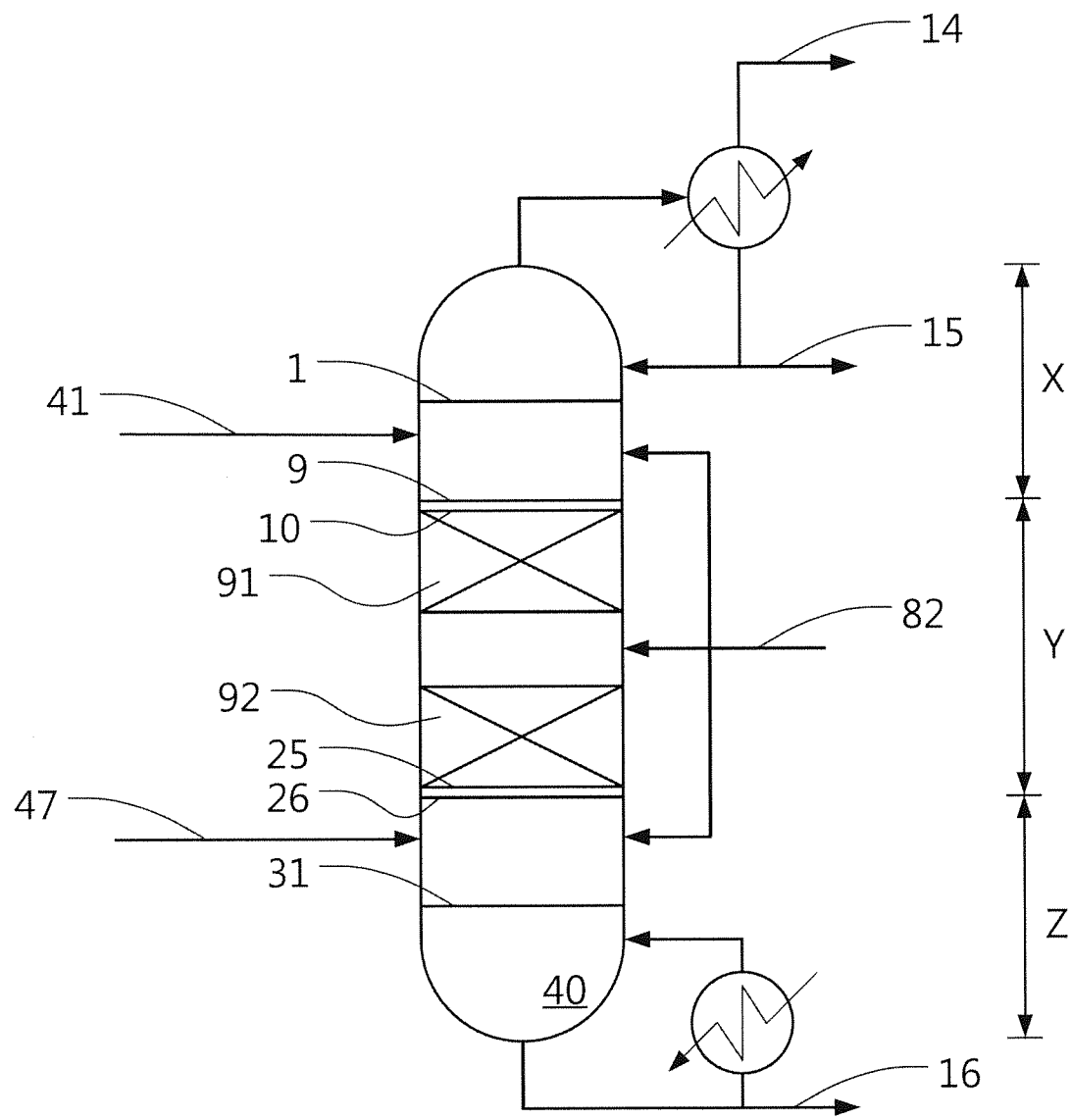
FIG. 1 shows schematic diagram of the catalytic distillation column for co-producing of MTBE and isobutene.

FIG. 1 is a schematic diagram of the column for co-production of MTBE and isobutene. The catalytic distillation (CD) column 40 contains a total of 31 trays, with additional reboiler and a total or partial condenser. The CD column is divided into three zones. The top zone is a rectification zone X, trays numbered from 1 to 9. Middle zone is a catalytic zone Y with an upper bed 91 and a lower bed 92, trays 10 to 25. The bottom zone is a stripping zone Z, trays 26 to 31. A single-bed catalyst or dual-bed catalysts can be applied to the catalytic zone Y. Moreover, in the dual-bed catalysts, the allowable operating temperature of an upper bed catalyst is lower than a lower bed catalyst. The catalytic zone Y comprises at least a solid acid catalyst, wherein the ion exchange resin with sulfonic acid group is particularly suitable in use. Said ion exchange resin with sulfonic acid group is characterized in having acid capacity more than 2.0 meq/g, e.g. Amberlyst® 15, Amberlyst® 35, Amberlyst® 70, Purolite® CT-275, Purolite® CT-482; where the maximum operating temperatures of these catalysts are in the order of Amberlyst 70 (190° C.), CT-482 (190° C.)>Amberlyst 35 (150° C.), CT-275 (130° C.)>Amberlyst 15 (120° C.) as recommended by resins suppliers. Other inorganic catalysts are acceptable and able to be used, e.g. aluminum silicon oxide which treated by fluoride, sulfuric acid, or sulfonic acid; or Y-type zeolite or HZSM-5 zeolite; or any combination thereof.

As shown in FIG. 1, the methanol/TBA mixture and additional methanol are charged to the rectification zone X and stripping zone Z via lines 41 and 47, respectively, wherein the concentration of the methanol is 0.1~40 wt %, and 2~20 wt % is preferred. The best location is above the upper bed 91 for TBA mixture and below the lower bed 92 for methanol. The excess methanol is recycled and fed to the CD column 40 via line 82. The position below the catalytic zone Y is preferred for high methanol concentration. In this way, TBA dehydration, methanol tert-butylation and isobutene etherification can occur simultaneously in the catalytic zone Y. Light products, isobutene and MTBE, will be withdrawn from the top of the CD column 40, lines 15 or 14. Heavy compounds, water and excess methanol, will be withdrawn from the bottom, line 16. By blending the fresh TBA with the required methanol or making up fresh methanol as an additional feed, this column design allows high flexibility to produce desirable isobutene-to-MTBE ratio. This is because the product of isobutene-to-MTBE ratio is partly dependent on the total methanol that is charged to the CD column 40.

Figure 2:
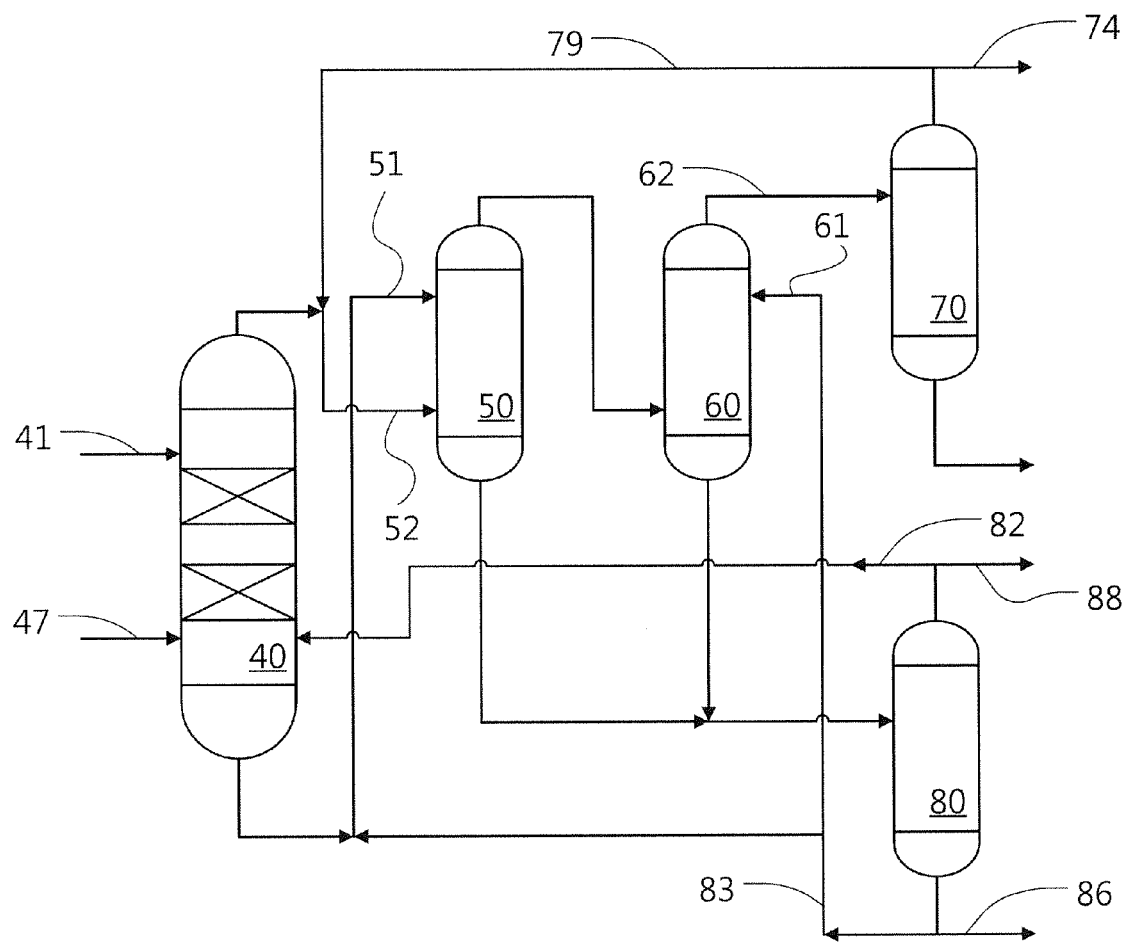
FIG. 2 shows a structural schematic diagram according to an embodiment co-producing isobutene and MTBE from TBA mixture.

FIG. 2 shows a structural schematic diagram according to an embodiment co-producing isobutene and MTBE from TBA mixture, where the columns connected by lines which made by pipes. Both feeds are charged to the CD column 40. One is the mixture of TBA and methanol from line 41 and another is the recycled high-methanol-concentration stream from line 82. For high MTBE yield, the make-up methanol is fed through line 47 to the CD column 40. The effluent from the top of the CD column 40 contains mostly isobutene and MTBE, which is oil-phased liquid, and contains few unreacted methanol, which is aqueous-phased liquid. This stream is fed to the first wash column 50 via line 52 to extract unreacted methanol. The extract solvent, water comes from the bottom of the CD column 40 or the bottom of the methanol recovery column 80 via lines 83 and 51. The oil phase stream, mainly isobutene, leaving the top of isobutene column 70 via lines 79 and 52 is used to enhance extraction efficiency, if necessary. The residual methanol in isobutene raffinate from the first wash column 50 shall be washed again in the second wash column 60 for achieving high purity isobutene. The extract solvent, high purity water coming from the bottom of the methanol recovery column 80 is fed to the second wash column 60 via lines 83 and 61. Both first and second wash columns may be combined into to one unitary wash column to save equipment cost.

Figure 3:
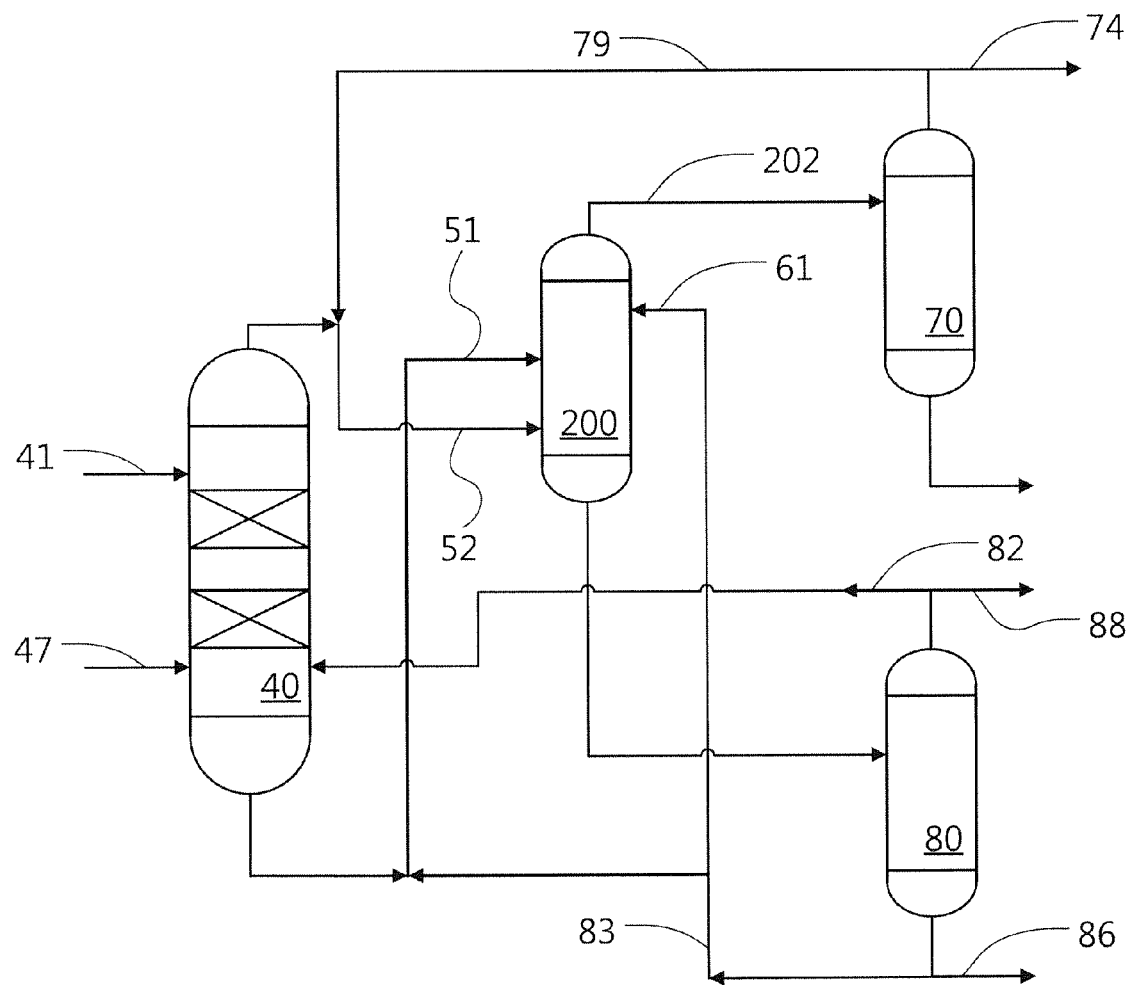
FIG. 3 shows a structural schematic diagram according to another embodiment combining the first wash column and the second wash column to a unitary wash column.

In the case of combining the first wash column 50 and the second wash column 60, please refer to FIG. 3, the unitary wash column 200 is similar to the structure that the second wash column 60 stacks on the first wash column 50. The unitary wash column 200 receives the effluent from the top of the CD column 40 to extract unreacted methanol. The extract solvent, water leaving the bottom of the CD column 40 or the bottom of the methanol recovery column 80 is fed to the unitary wash column 200 via lines 83, 51 and 61. The raffinate from the unitary wash column 200 is fed to the isobutene column 70 via line 202.

The raffinate from the second wash column 60 or above said unitary wash column 200 is mainly composed of isobutene and MTBE. It is fed to the isobutene column 70 via line 62 (as shown in FIG. 2) or line 202 (as shown in FIG. 3). isobutene is distillated from the top of the isobutene column 70. Part of isobutene can be recycled to the wash columns and part is sent through line 74 as the primary product isobutene. The methanol and water rich mixture from wash columns is sent to the methanol recovery column 80. The recovered methanol-rich mixture is recycled through line 82 and excess is sent through line 88 to storage tank. The bottom product is high purity water, a portion is recycled as wash water via line 83 and the other portion is sent to wastewater treatment plant via line 86.

Figure 4:
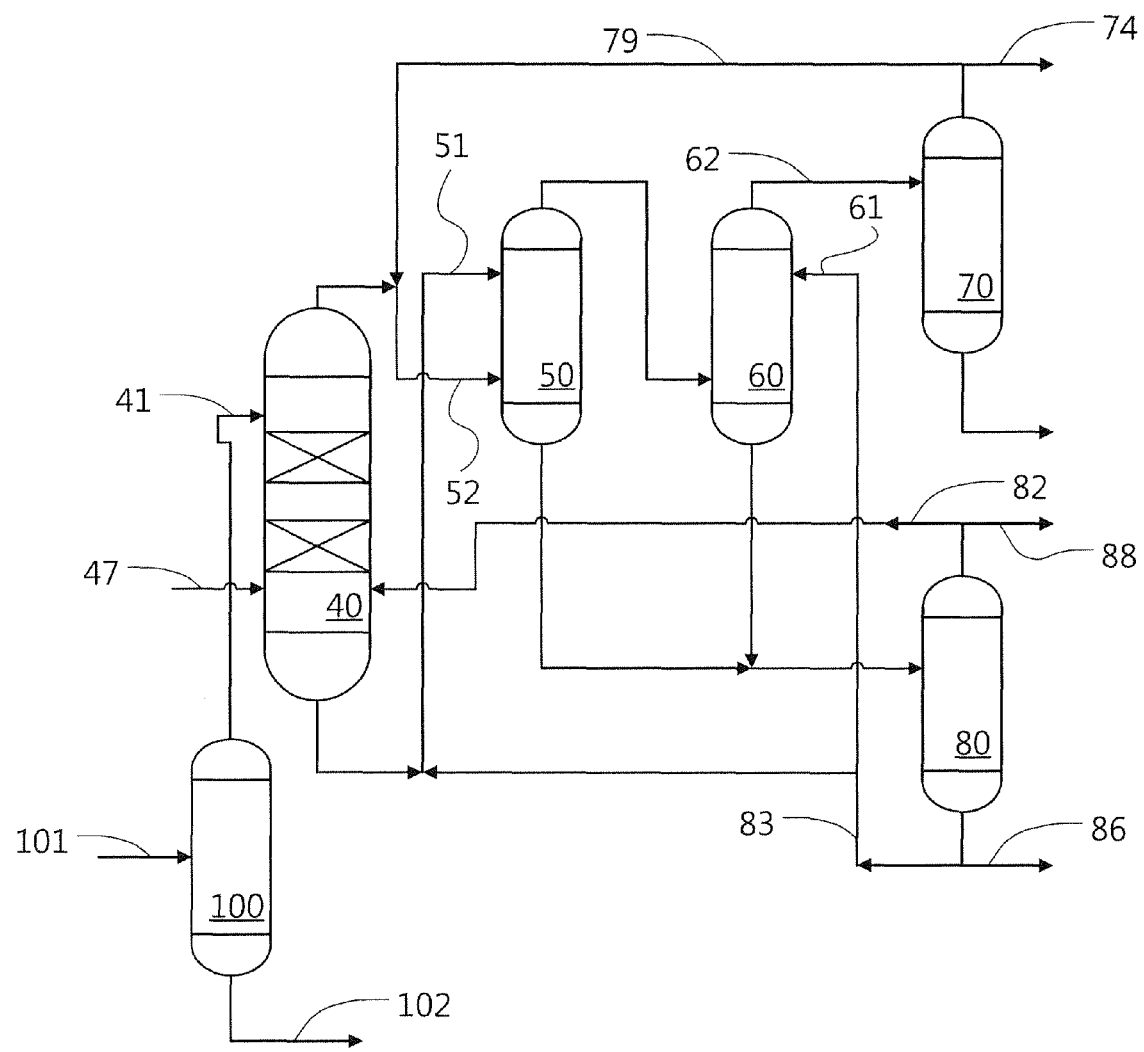
FIG. 4 shows a structural schematic diagram according to still another embodiment co-producing isobutene and MTBE from TBA mixture.

FIG. 4 shows another embodiment co-producing isobutene and MTBE from TBA mixture, which contaminates with butanol isomers. The impurities in crude TBA coming from the PO process are mainly isobutanol and 2-butanol as disclosed in U.S. Pat. No. 5,625,109. Because the boiling point of TBA is the lowest among butanol isomers, the TBA mixture priorly charged to the CD column 40 can be fed through line 101 and distilled in a de-butanol column 100 to remove the heavier isomers from the bottom of the column via line 102. Thus, the impact of butanol isomers on the invented process can be minimized and the CD column 40, wash columns 50, 60, isobutene column 70 and methanol recovery column 80 still can work well.

The following examples show the effects of the operating variables from simulation with a commercial software, ASPEN PLUS. The model input parameters are summaried as follows. To the best of our knowledge, 640 kt/a of TBA is produced as a by-product at a typical 240 kt/a propylene oxide plant. The quantity corresponding to the TBA feed rate to the CD column 40 in FIG. 2 is about 80 ton/hr. Including one reboiler and one condenser, there are 33 theoretical plates in the CD column model, numbered from top to bottom. The catalytic zone is configured between plates 11 and 26. The TBA or TBA mixture is fed above plate 10 at 60° C. The recycled methanol mixture and make-up methanol are fed above plate 27 at 70° C. The catalyst volume per tray in the catalytic zone is assumed to be 15% of tray space. The diameter of the CD column is dependent on the operating parameters, such as column pressure, methanol-to-TBA molar ratio, reflux ratio, distillate-to-feed ratio. The default sieve tray sizing equation in ASPEN PLUS is selected for calculations. The rate equations for calculating reaction rates are adopted from the work of Matouq et al. (Kinetics of Liquid Phase Synthesis of Methyl tert-Butyl Ether from tert-Butyl Alcohol and Methanol Catalyzed by Ion Exchange Resin, International Journal of Chemical Kinetics, 25 (10), 825-831, 1993.). The default UNIQUAC and UNIFAC-LL method in the ASPEN PLUS software are used to compute vapor-liquid and liquid-liquid equilibrium compositions, respectively. With these operating parameters, the CD column model can be solved to obtain the information on isobutene and MTBE product streams.

In the present invention, the operating parameters of the CD column defined as: column pressure is set at 1.5~7 kg/cm², preferred is 3~5 kg/cm²; temperature profile is between 20~160° C., preferred is 40~145° C.; methanol-to-TBA molar ratio, reflux ratio, and distillated-to-feed ratio are 0.1~5, 1~10, 0.3~0.9, respectively, preferred are 0.2~1.5, 1~4, and 0.6~0.85.

The TBA conversion and isobutene selectivity are defined as following equations.

$$X_{TBA} = 1 - F_{out}/F_{in}|_{TBA}$$

$$S_{IB} = F_{IB}/(F_{Ib} + F_{MTBE})|_{out}$$

In above equations, the F is molar flow, in/out is the inlet/outlet of the CD column and TBA/IB/MTBE is TBA/isobutene/MTBE.

EXAMPLE 1

The solid state TBA (Merck reagent grade, >99.5%) is melted in a water bath at constant temperature of 45° C. 126.1 gram of TBA is weighted and put into a 500 mL of erlenmeyer flask and 6.3 gram of methanol (Merck reagent grade, >99.9%) is added to the TBA. A clear and transparent solution is obtained. The methanol concentration is 4.76 wt %. A rubber stopper attached to an alcohol thermometer is used to plug the flask. The flask is moved to a refrigerator circulated with ethanol and gradually cooled down from 20° C. The flask is shaked from time to time. The freezing temperature is decreased 0.5° C. for each time after temperature reaches equilibrium between coolant and the solution. Carefully observe the thermometer and if crystal is formed. Record the crystallizing-out temperature. Repeat two times to measure the cloud point of the TBA mixture. The cloud points of TBA mixed with 8.22 wt % and 10.5 wt % of methanol are measured with the above mentioned procedure. Results are summarized in Table 1. It can be seen that the cloud point decreases by 3.86° C. if the methanol concentration is increased by 1%.

TABLE 1

| | Methanol, wt % | | | | | | | |
|---|---|---|---|---|---|---|---|---|
| | 4.758 | | | 8.224 | | | 10.504 | |
| Test no. | 1 | 2 | 3 | 1 | 2 | 3 | 1 | 2 | 3 |
| Cloud point, ° C. | 8 | 8.5 | 8.3 | −5.5 | −5.0 | −5.5 | −14 | −14.2 | −13.5 |

EXAMPLE 2

A 13%/45%/40% methanol/TBA/water mixture was charged in the reboiler of a pilot-scale catalytic distillation column. The inside diameter of the column was 3 inches and the height was 19 feet. The reaction section was in the middle of the column which was loaded with 427 g of dry Amberlyst 35. Before start-up, the system was blanketed with nitrogen at 1.38 kg/cm².

When reboiler was heated, the column pressure was controlled at 3.16 kg/cm². After the column reached the steady state at total reflux for one hour, a 80%/20% TBA/methanol mixture was continuously fed above the catalytic zone. The reflux was started and the rate was controlled at 0.8 kg/hr and the control for liquid level across reboiler was turned on. After the column was operated for six hours, six samples were taken. The sampling points are S-1, S-2, S-3 and S-4, which corresponded to 1, 5, 9 and 15 feet high above the reboiler, respectively. Other two samples, S-Top and S-Btm, were taken at the outlet of the condenser and reboiler. Before sampling, the recorded hourly averaged feed rate, distillate and reflux rate are 1.12 kg/hr, 0.68 kg/hr and 0.86 kg/hr. Column temperature profiles are shown in FIG. 5.

The samples were analyzed with a gas chromatograph (Agilent Technologies Model 6890 N, TCD model) coupled with the ChemStation software. A capillary column (J&W DB-WAX, 30 m*0.32 mm i.d., 0.5 μm phase film) was used with He flowing at 25 cm/s, starting at 40° C. for 5 min and then increasing at a 10° C./min temperature-programming rate until it reached 100° C. for 1 min (0.5 μl split 40:1). The temperature at injection port and detector was set at 240 and 250° C., respectively.

Figure 5:
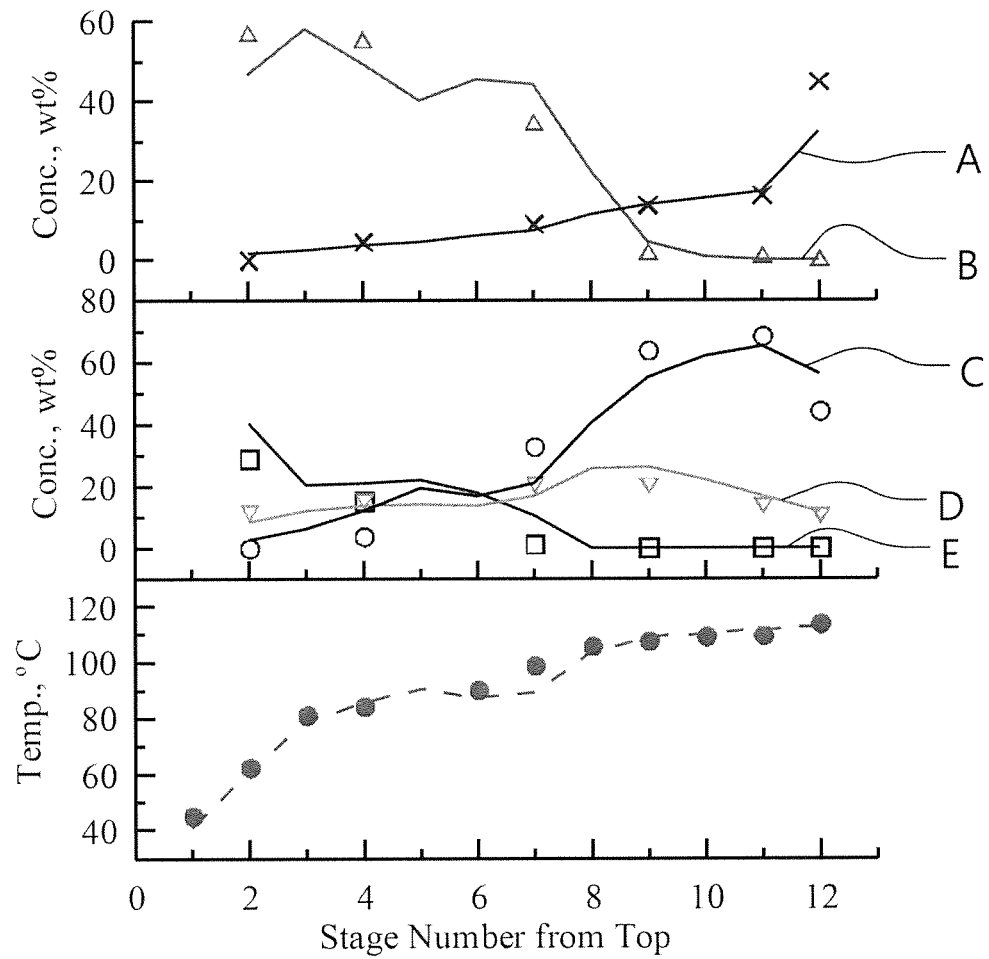
FIG. 5 shows the experiment results of a pilot-scale catalytic distillation column.

The analysis results are also shown in FIG. 5. In FIG. 5, number A--E represents water, MTBE, TBA, methanol, and isobutene respectively. It can been seen that the concentration of methanol/TBA/water mixture in the reboiler (S-Btm) changes from 13%/45%/40% at the beginning to 11%/44%/45% at the end of operation. Significant amount of MTBE is observed at the point (S-4) above the catalyst bed. The mass ratio of isobutene-to-MTBE of the distillate (S-Top) reached 0.94. These results prove that TBA and methanol contacting with acid resin Amberlyst 35 can co-produce MTBE and isobutene in the catalytic distillation column.

The solid line in FIG. 5 was modeled according to the operating data, pressure=3.16 kg/cm², reflux ratio=1.2647, distillate-to-feed ratio=0.6071. Modeling results are fairly consistent with the column temperature and the component analysis data. This set-up model was then used to explore the co-production process of isobutene and MTBE from TBA in Examples 3 to 12.

EXAMPLE 3

This example is a base case for exploring the effects of operating parameters on isobutene selectivity.

Column pressure is set at 3.03 kg/cm² and total condenser is subcooled at 40° C. The molar ratio of methanol to TBA is 1.0. As reflux ratio and distillate to feed mass ratio are 3.0 and 0.78, the column size can be determined by these column parameters. Then, the calculated catalyst volume per tray is 0.676 m³. The calculated reaction temperature at the catalytic zone is 96.3-99.7° C. The TBA conversion and isobutene selectivity is 99.97% and 51.2%.

EXAMPLE 4

This example demonstrates the effect of high methanol to TBA molar ratio on TBA conversion.

Column pressure is set at 3.03 kg/cm$^2$ and total condenser is subcooled at 40° C. The molar ratio of methanol to TBA increases to 1.5. As reflux ratio and distillate to feed mass ratio are 3.0 and 0.83, the column size can be determined by these column parameters. Then, the calculated catalyst volume per tray is 0.728 m$^3$. The calculated reaction temperature at the catalytic zone is 97.4-98.6° C. The TBA conversion and isobutene selectivity is 99.95% and 46.1%.

The effect of higher molar ratio to improve MTBE yield is limited.

EXAMPLE 5

This example demonstrates the effect of reduced column pressure on TBA conversion.

Column pressure is set at 1.53 kg/cm$^2$ and partial condenser is cooled at 40° C. The molar ratio of methanol to TBA is 1.0. As reflux ratio and distillate to feed mass ratio are 4.0 and 0.4, the column size can be determined by these column parameters. Then, the calculated catalyst volume per tray is 0.609 m$^3$. The calculated reaction temperature at the catalytic zone is 71.0-82.2° C. The TBA conversion and isobutene selectivity is 62.4% and 68.0%.

Both vapor and liquid products from the condenser are mainly mixture of isobutene and MTBE. Lower column pressure is not efficient to separate isobutene and MTBE in the partial condenser. Also, TBA conversion decreases significantly.

EXAMPLE 6

This example demonstrates the effect of higher column pressure and lower methanol to TBA molar ratio on TBA conversion.

Column pressure is set at 4.53 k g/cm$^2$ and total condenser is subcooled at 40° C. The molar ratio of methanol to TBA decreases to 0.25. As reflux ratio and distillate to feed mass ratio are 2.5 and 0.74, the column size can be determined by these column parameters. Then, the calculated catalyst volume per tray is 0.523 m$^3$. The calculated reaction temperature at the catalytic zone is 98.7-113.6° C. The TBA conversion and isobutene selectivity is 99.98% and 91.2%.

Higher pressure not only results in higher column temperature but also results in higher reaction rate. Due to lower molar ratio and reflux ratio, both TBA and MTBE decompose on the upper zone of CD trays. The reverse etherification results in higher isobutene selectivity and the product isobutene does not inhibit TBA dehydration.

EXAMPLE 7

Comparing with Example 3, the feed above catalytic zone is TBA mixture rather than pure TBA. Thus, the fresh TBA mixture can be shipped anywhere in the world. The methanol concentration is 17.8 wt %. To keep the same methanol to TBA molar ratio as in Example 3, the amount of methanol fed below the catalytic zone is half of that in Example 3.

Operating parameters are the same as those in Example 3. Column pressure is set at 3.03 kg/cm$^2$ and total condenser is subcooled at 40° C. The molar ratio of methanol to TBA is LO. The reflux ratio and distillate to feed mass ratio are 3.0 and 0.78, and the catalyst volume per tray is 0.676 m$^3$. The calculated reaction temperature at the catalytic zone is 91.2-98.9° C. The TBA conversion and isobutene selectivity is 99.78% and 51.2%.

Isobutene selectivity is influenced by the feed concentration of the TBA mixture, but TBA conversion is not.

EXAMPLE 8

Comparing with Example 6, the feed above catalytic zone is TBA mixture rather than pure TBA. The methanol concentration is 5.1 wt %. To keep the same methanol to TBA molar ratio as in Example 6, the amount of methanol fed below the catalytic zone is half of that in Example 6.

Operating parameters are the same as those in Example 6. Column pressure is set at 4.53 kg/cm$^2$ and total condenser is subcooled at 40° C. The molar ratio of methanol to TBA is 0.25. The reflux ratio and distillate to feed mass ratio are 2.5 and 0.74, and the catalyst volume per tray is 0.523 m$^3$. The calculated reaction temperature at the catalytic zone is 98.0-113.4° C. The TBA conversion and isobutene selectivity is 99.95% and 92.4%.

TBA conversion and isobutene selectivity are slightly influenced by the feed concentration of the TBA mixture.

Table 2 summarizes the operating parameters of the CD column for Examples 3-8, and their effects on TBA conversion and isobutene selectivity. Table 3 is the product data of the CD column for Examples 3-8.

TABLE 2

Operating parameters: $N_{total}$ = 33, $N_{TBA}$ = 10, $N_{MeOH}$ = 27, $N_{cat}$ = 11-26, $T_{TBA}$ = 60° C., $T_{MeOH}$ = 70° C.

| | Ex 3 | Ex 4 | Ex 5 | Ex 6 | Ex 7 | Ex 8 |
|---|---|---|---|---|---|---|
| Pressure, kg/cm$^2$ | 3.03 | 3.03 | 1.53 | 4.53 | 3.03 | 4.53 |
| MeOH/TBA molar ratio | 1.0 | 1.5 | 1.0 | 0.25 | 1.0 | 0.25 |
| $T_{condenser}$, ° C. | 40 | 40 | 40 | 40 | 40 | 40 |
| Reflux ratio | 3 | 3 | 4 | 2.5 | 3 | 2.5 |
| Distillate to feed ratio | 0.78 | 0.83 | 0.4 | 0.74 | 0.78 | 0.74 |
| Cat. vol. per tray, m$^3$ | 0.676 | 0.728 | 0.609 | 0.523 | 0.676 | 0.523 |
| TBA purity, wt % | 100 | 100 | 100 | 100 | 82.2 | 94.9 |
| TBA conversion, % | 99.97 | 99.95 | 62.4 | 99.98 | 99.78 | 99.95 |
| Isobutene selectivity, % | 51.2 | 46.1 | 68.0 | 91.2 | 51.2 | 92.4 |

TABLE 3

Product data of the CD column

| | stream no. | flow ton/hr | weight fraction iC$_4^-$ | MTBE | MeOH | TBA | H$_2$O |
|---|---|---|---|---|---|---|---|
| Ex 3 | 15 (top) | 89.4 | 0.347 | 0.519 | 0.130 | 0.0 | 0.004 |
| | 16 (bottom) | 25.2 | 0.0 | 0.0 | 0.242 | 0.001 | 0.757 |
| Ex 4 | 15 (top) | 109.5 | 0.255 | 0.469 | 0.276 | 0.0 | 0.0 |
| | 16 (bottom) | 22.4 | 0.0 | 0.0 | 0.134 | 0.001 | 0.864 |
| Ex 5 | 14 (top$_{Vap}$) | 45.4 | 0.565 | 0.411 | 0.011 | 0.0 | 0.013 |
| | 15 (top$_{Liq}$) | 0.39 | 0.137 | 0.834 | 0.015 | 0.002 | 0.013 |
| | 16 (bottom) | 68.8 | 0.0 | 0.0 | 0.395 | 0.437 | 0.168 |
| Ex 6 | 15 (top) | 65.6 | 0.842 | 0.128 | 0.021 | 0.0 | 0.01 |
| | 16 (bottom) | 23.0 | 0.0 | 0.0 | 0.182 | 0.001 | 0.817 |
| Ex 7 | 15 (top) | 89.4 | 0.346 | 0.518 | 0.132 | 0.0 | 0.003 |
| | 16 (bottom) | 25.2 | 0.0 | 0.0 | 0.235 | 0.007 | 0.758 |
| Ex 8 | 15 (top) | 65.6 | 0.853 | 0.110 | 0.030 | 0.0 | 0.008 |
| | 16 (bottom) | 23.0 | 0.0 | 0.0 | 0.177 | 0.002 | 0.821 |

EXAMPLE 9

This example demonstrates a co-production process for isobutene and MTBE, where the TBA mixture is used as feed and no make-up methanol. Considering the transportation feasibility, the methanol concentration in the mixture is 10.5 wt %. The freezing point of the mixture is below −12° C., same as that in Example 1.

The TBA mixture is fed above plate number 9 at 60° C. via line 41. The recycled methanol mixture is fed above plate number 26 at 70° C. via line 82. The methanol-to-TBA molar ratio of the CD column is 0.5485. Other operating parameters of the CD column are described below. Column pressure is set at 4.23 kg/cm$^2$ and total condenser is subcooled at 40° C. As reflux ratio and distillate to feed mass ratio are 2.24 and 0.78, the column size can be determined by these column parameters.

Then, the calculated catalyst volume per tray is 0.576 m$^3$. The calculated reaction temperature at the catalytic zone is 98.4-110.5° C. The TBA conversion and isobutene selectivity is 99.9% and 73.6%.

Other unit parameters are given below. The water-to-methanol molar ratio of the first wash column is 3.52. Column pressure is 9.03 kg/cm$^2$ and temperature is about 41° C. The theoretical plate numbers in the first wash column model are 5. The water-to-methanol molar ratio of the second wash column is 10.2. Column pressure is 8.53 kg/cm$^2$ and temperature is about 39° C. The theoretical plate numbers in the second wash column model are 5, too. Isobutene column pressure is set at 5.53 kg/cm$^2$ and total condenser is subcooled at 40° C. Theoretical plates, feed location, reflux ratio and distillate to feed mass ratio in this column model are 11, 4, 1.696 and 0.637, and further comprising a reboiler and a condenser. Methanol recovery column pressure is set at 2.53 kg/cm$^2$ and total condenser is subcooled at 40° C. Theoretical plates, feed location, reflux ratio and distillate to feed mass ratio in this column model are 23, 9, 2.58 and 0.294, and further comprising a reboiler and a condenser. Table 4 shows the modeling results for the streams as shown in FIG. 2.

TABLE 4 stream data for Example 9

| | Stream number | | | | | | | |
|---|---|---|---|---|---|---|---|---|
| | 41 | 82 | 83 | 74 | 75 | 86 | 47 | 88 | 79 |
| ton/hr wt % | 89.4 | 12.4 | 10.8 | 44.8 | 25.6 | 19.0 | 0 | 0 | 0 |
| Isobutene | 0 | 11.22 | 0 | 99.34 | 0.09 | 0 | 0 | 0 | 0 |
| MTBE | 0 | 11.16 | 0 | 0.03 | 98.23 | 0 | 0 | 0 | 0 |
| Methanol | 10.5 | 77.19 | 0.04 | 0.38 | 0.31 | 0.04 | 0 | 0 | 0 |
| TBA | 89.5 | 0.06 | 0 | 0 | 0.28 | 0 | 0 | 0 | 0 |
| Water | 0 | 0.36 | 99.96 | 0.26 | 1.09 | 99.96 | 0 | 0 | 0 |

EXAMPLE 10

This example demonstrates a co-production process for isobutene and MTBE, where the TBA mixture is used as feed and make-up methanol is used as second feed to increase MTBE yield as shown in FIG. 2, line 47. The methanol concentration in the TBA mixture is also 10.5 wt %.

The TBA mixture is fed above plate number 9 at 60° C. via line 41. Combining the make-up and recycled methanol from line 47 and 82, the mixture is fed above plate number 26 at 70° C. The methanol-to-TBA molar ratio of the CD column is 1.0. Other operating parameters of the CD column are described below. Column pressure is set at 2.73 kg/cm$^2$ and total condenser is subcooled at 40° C. As reflux ratio and distillate to feed mass ratio are 3.0 and 0.82, the column size can be determined by these column parameters. Then, the calculated catalyst volume per tray is 0.725 m$^3$. The calculated reaction temperature at the catalytic zone is 92.3-95.9° C. The TBA conversion and isobutene selectivity is 99.9% and 46.4%.

Other unit parameters are given below. The water-to-methanol molar ratio of the first wash column is 2.15. Column pressure is 9.03 kg/cm$^2$ and temperature is about 40° C. The theoretical plate numbers in the first wash column model are 5. The water-to-methanol molar ratio of the second wash column is 8.48. Column pressure is 8.53 kg/cm$^2$ and temperature is about 40° C. The theoretical plate numbers in the second wash column model are 5, too. Isobutene column pressure is set at 5.53 kg/cm$^2$ and total condenser is subcooled at 40° C. Theoretical plates, feed location, reflux ratio and distillate to feed mass ratio in this column model are 11, 4, 0.972 and 0.618, and further comprising a reboiler and a condenser. Methanol recovery column pressure is set at 2.13 kg/cm$^2$ and total condenser is subcooled at 40° C. Theoretical plates, feed location, reflux ratio and distillate to feed mass ratio input in this column model are 28, 14, 1.243 and 0.334, and further comprising a reboiler and a condenser. Table 5 shows the modeling results of the streams as shown in FIG. 2.

TABLE 5 stream data for Example 10

| | Stream number | | | | | | | |
|---|---|---|---|---|---|---|---|---|
| | 41 | 82 | 83 | 74 | 75 | 86 | 47 | 88 | 79 |
| ton/hr wt % | 89.4 | 21.2 | 23.4 | 28.3 | 51.7 | 18.8 | 9.46 | 0 | 55.5 |
| Iso-butene | 0 | 12.39 | 0 | 99.14 | 0.08 | 0 | 0 | 0 | 99.14 |
| MTBE | 0 | 12.93 | 0 | 0.09 | 98.36 | 0 | 0 | 0 | 0.09 |

TABLE 5-continued stream data for Example 10

| | Stream number | | | | | | | |
|---|---|---|---|---|---|---|---|---|
| | 41 | 82 | 83 | 74 | 75 | 86 | 47 | 88 | 79 |
| Methanol | 10.5 | 74.28 | 0.06 | 0.39 | 0.44 | 0.06 | 100.0 | 0 | 0.39 |
| TBA | 89.5 | 0.05 | 0 | 0 | 0.14 | 0 | 0 | 0 | 0 |
| Water | 0 | 0.36 | 99.94 | 0.37 | 0.98 | 99.94 | 0 | 0 | 0.37 |

EXAMPLE 11

This example demonstrates a co-production process for isobutene and MTBE, where the TBA mixture contaminated with isobutanol, 2-butanol and water is used as feed and no make-up methanol. Before mixed with methanol, the crude TBA (94.5wt %) coming from the PO process perhaps contains 1.1% water and 4.4% isobutanol (with reference to U.S. Pat. No. 5,625,109). To our best knowledge, the impurities are mainly water, isobutanol, 2-butanol or 1-butanol. In this example, 4.4% butanol isomers are divided into 2.2% isobutanol and 2.2% 2-butanol. The methanol concentration in the TBA mixture is maintained at 10.71 wt % almost as same as in Example 9.

The de-butanol column parameters are given below. Column pressure is set at 0.68 kg/cm$^2$ and total condenser is cooled at saturated temperature. Theoretical plates, feed location, reflux ratio and distillate to feed mass ratio in this column model are 33, 17, 1.5 and 0.9607, and further comprising a reboiler and a condenser. Simulation results show that anhydrous mixture of isobutanol and 2-butanol can be removed from the bottom effluent and water together with TBA and methanol will go through the top of the column. The anhydrous butanol mixture can be further separated to high purity chemicals or directly used as fuel additives.

Then, the top effluent of the de-butanol column is fed above plate number 9 of the CD column at 60° C. via line 41. The recycled methanol mixture is fed above plate number 26 at 70° C. via line 82. The methanol-to-TBA molar ratio of the CD column is 0.5725. Other operating parameters of the CD column are described below. Column pressure is set at 4.53 kg/cm$^2$ and total condenser is cooled at saturated temperature. As reflux ratio and distillate to feed mass ratio are 1.6 and 0.7805, the column size can be determined by these column parameters. Then, the calculated catalyst volume per tray is 0.4763 m$^3$. The calculated reaction temperature at the catalytic zone is 102.2-113.7° C. The TBA conversion and isobutene selectivity is 99.9% and 70.9%.

Other unit parameters are given below. The water-to-methanol molar ratio of the first wash column is 3.72. Column pressure is 9.03 kg/cm$^2$ and temperature is about 40° C. The theoretical plate numbers in the first wash column model are 5. The water-to-methanol molar ratio of the second wash column is 14.3. Column pressure is 8.53 kg/cm$^2$ and temperature is about 39° C. The theoretical plate numbers in the second wash column model are 5, too. Isobutene column pressure is set at 6.03 kg/cm$^2$ and total condenser is cooled at saturated temperature. Theoretical plates, feed location, reflux ratio and distillate to feed mass ratio in this column model are 11, 4, 1.993 and 0.606, and further comprising a reboiler and a condenser. Methanol recovery column pressure is set at 2.58 kg/cm$^2$ and total condenser is cooled at saturated temperature. Theoretical plates, feed location, reflux ratio and distillate to feed mass ratio in this column model are 23, 11, 3.34 and 0.262, and further comprising a reboiler and a condenser. Table 6 shows the modeling results for the streams as shown in FIG. 4.

TABLE 6 stream data for Example 11

| | Stream number | | | | | | | |
|---|---|---|---|---|---|---|---|---|
| | 101 | 102 | 41 | 82 | 83 | 74 | 75 | 86 | 47/88/79 |
| ton/hr | 89.6 | 3.52 | 86.08 | 11.83 | 14.41 | 40.76 | 26.47 | 18.86 | 0 |
| wt % | | | | | | | | | |
| Isobutene | 0 | 0 | 0 | 10.9 | 0 | 99.45 | 0.08 | 0 | 0 |
| MTBE | 0 | 0 | 0 | 11.76 | 0 | 0.03 | 98.62 | 0 | 0 |
| Methanol | 10.71 | 0 | 11.5 | 77.0 | 0.02 | 0.18 | 0.13 | 0.02 | 0 |
| TBA | 84.38 | 0.06 | 87.82 | 0.09 | 0 | 0 | 0.22 | 0 | 0 |
| Water | 0.98 | 0 | 1.02 | 0.25 | 99.98 | 0.33 | 0.95 | 99.98 | 0 |
| 2-butanol | 1.96 | 49.98 | 0 | 0 | 0 | 0 | 0 | 0 | 0 |
| Isobutanol | 1.96 | 49.98 | 0 | 0 | 0 | 0 | 0 | 0 | 0 |

EXAMPLE 12

This example demonstrates a co-production process for isobutene and MTBE, where the first wash column and the second wash column are combining into a unitary wash column 200 as shown in FIG. 3.

Comparing with example 9, the operating parameters of the unitary wash column are given below. Column pressure is 8.53 kg/cm$^2$ and temperature is about 40° C. The theoretical plate numbers in the unitary wash column model are 10. The line 61 is fed to the plate 1 (Top), the line 51 fed to the plate 6, and the isobutene mixture in oil phase is fed to the plate 10 (bottom).

The flow rate, composition, temperature, and pressure of the material fed to the unitary wash column 200 via the line 51, 52, and 61 are same with example 9. After calculation, the line 202 in example 12 and the line 62 in example 9, where the outcome of the washed oil phase isobutene mixture are shown in Table 7. The combination of the first wash column and the second wash column does not affect the washing result.

TABLE 7 stream data for Example 12

| | Stream number | | | | |
|---|---|---|---|---|---|
| | 61 | 51 | 52 | 62 | 202 |
| ton/hr | 10.8 | 22.4 | 79.4 | 70.4 | 70.5 |
| wt % | | | | | |
| Isobutene | 0 | 0 | 57.81 | 63.26 | 63.26 |
| MTBE | 0 | 0 | 33.39 | 35.71 | 35.76 |
| Methanol | 0.04 | 15.79 | 7.94 | 0.36 | 0.31 |
| TBA | 0 | 0.35 | 0 | 0.1 | 0.11 |
| Water | 99.96 | 83.87 | 0.87 | 0.56 | 0.56 |

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

What is claimed is:

1. A method for coproducing isobutene and methyl tert-butyl ether (MTBE) from tert-butanol (TBA) mixture, comprising steps:
   feeding TBA mixture, wherein the TBA mixture includes TBA and methanol, into a rectification zone of a catalytic distillation column;
   feeding methanol into a stripping zone of the catalytic distillation column; and
   catalyzing the TBA mixture and the methanol in a catalytic zone of the catalytic distillation column to make the dehydration of the TBA of the TBA mixture and the etherification of the TBA with methanol occur simultaneously, and
   isobutene and MTBE are co-produced;
   wherein the catalytic distillation column is distinguished into the rectification zone, the catalytic zone, and a stripping zone from the top down.

2. The method as claimed in claim 1, wherein the concentration of the methanol is 0.1~40 wt %.

3. The method as claimed in claim 1, wherein the concentration of the methanol is 2~20 wt %.

4. The method as claimed in claim 1, wherein the catalytic zone having at least a catalyst, where the catalyst is a solid acid catalyst.

5. The method as claimed in claim 4, wherein the catalyst in the catalytic zone is ion exchange resin with sulfonic acid group, the ion exchange resin with sulfonic acid group having acid capacity more than 2.0 meq/g.

6. The method as claimed in claim 4, wherein the catalytic zone comprises a single-bed catalyst or a dual-bed catalysts, where in the dual-bed catalysts, the allowable operating temperature of an upper bed catalyst is lower than the allowable operating temperature of a lower bed catalyst.

7. The method as claimed in claim 1, wherein the column pressure of the catalytic distillation column is 1.5~7 kg/cm$^2$.

8. The method as claimed in claim 1, wherein the temperature profile of the catalytic distillation column is 20~160° C.

9. The method as claimed in claim 1, wherein the methanol-to-TBA molar ratio in the catalytic distillation column is 0.1~5.

10. The method as claimed in claim 1, wherein the reflux ratio in the catalytic distillation column is 1~10.

11. The method as claimed in claim 1, wherein the distillated-to-feed ratio in the catalytic distillation column is 0.3~0.9.

12. The method as claimed in claim 1, wherein after the step of catalyzing the TBA mixture and the methanol in the catalytic zone of the catalytic distillation column, further comprising step:
   washing and distilling a product of the catalytic distillation column to purify isobutene and MTBE, and recycle methanol.

13. The method as claimed in claim 12, wherein in the step of washing and distilling the product of the catalytic distillation column, further comprising steps:
   feeding the product of the catalytic distillation column into a first wash column to make the methanol change into aqueous-phased, and purifying a oil-phased isobutene and MTBE; and
   distilling the oil-phased isobutene and MTBE to separate isobutene and MTBE, and distilling the aqueous-phased methanol.

14. The method as claimed in claim 13, wherein in the catalytic distillation column further connects with the first wash column, the first wash column extracts unreacted methanol and recycles the unreacted methanol to the catalytic distillation column.

15. The method as claimed in claim 14, wherein the first wash column, further connects with a second wash column, and the second wash column extracts a raffinate from the first wash column.

16. The method as claimed in claim 15, wherein the second wash column further connects with an isobutene column, where the isobutene column distills the oil-phased isobutene and MTBE to separate isobutene and MTBE.

17. The method as claimed in claim 15, wherein the first wash column and the second wash column further connect with a methanol recovery column.

18. The method as claimed in claim 17, wherein an aqueous-phased liquid fed into the first wash column comes from the bottom of the catalytic distillation column or the bottom of the methanol recovery column.

19. The method as claimed in claim 17, wherein an aqueous-phased liquid fed into the second wash column comes from the bottom of the methanol recovery column.

20. The method as claimed in claim 17, wherein an oil-phased liquid fed into the first wash column comes from the top of the catalytic distillation column or the top of the isobutene column.

* * * * *